United States Patent [19]

Bond et al.

[11] Patent Number: 4,601,468
[45] Date of Patent: Jul. 22, 1986

[54] EXERCISE AND DIAGNOSTIC SYSTEM AND METHOD

[75] Inventors: Malcolm L. Bond, Winters; Philip T. Dempster, St. Helena, both of Calif.

[73] Assignee: Loredan Biochemical, Inc., Davis, Calif.

[21] Appl. No.: 568,751

[22] Filed: Jan. 6, 1984

[51] Int. Cl.⁴ ............................................. A63B 21/00
[52] U.S. Cl. .................................. 272/130; 272/129; 272/143; 272/DIG. 6; 128/25 R
[58] Field of Search .................... 128/774, 782, 25 R; 272/130, 132, 143, 129, 125, DIG. 6

[56] References Cited

U.S. PATENT DOCUMENTS

| | | | |
|---|---|---|---|
| 3,465,592 | 9/1969 | Perrine | 272/130 |
| 3,895,623 | 7/1975 | Mahlandt et al. | 128/25 R |
| 4,063,726 | 12/1977 | Wilson | 272/130 |
| 4,247,098 | 1/1981 | Brentham | 272/130 |
| 4,436,099 | 3/1984 | Raftopoulos | 128/774 |

*Primary Examiner*—Richard C. Pinkham
*Assistant Examiner*—Leo P. Picard
*Attorney, Agent, or Firm*—Flehr, Hohbach, Test, Albritton & Herbert

[57] ABSTRACT

A muscle exercise and diagnostic system which includes a lever arm, a mounting arrangement for mounting the lever arm for rotation about a fixed axis, and a connecting arrangement for connecting a selected portion of the human body to the lever arm for rotation with the lever arm about a selected anatomical axis of rotation. The connecting arrangement establishes a fixed tangential mounting relation and a sliding radial mounting relation between the lever arm and the body portion. This permits free radial movement of the connecting arrangement relative to the fixed axis during an exercise motion. A velocity control arrangement is coupled to the lever arm for limiting the maximum permitted rotational velocity to a value predetermined in accordance with a preselected velocity control function which includes measured values of the distances from the point of attachment to the anatomical axis and to the fixed axis. An arrangement is provided for inputting these measured values to the velocity control arrangement. One such arrangement continuously registers with a potentiometer the distance from the connection point to the fixed axis and supplies that registered distance value to the velocity control computer. The measured value of distance from connection point to anatomical axis is input by a manual dial connected to a potentiometer.

20 Claims, 14 Drawing Figures

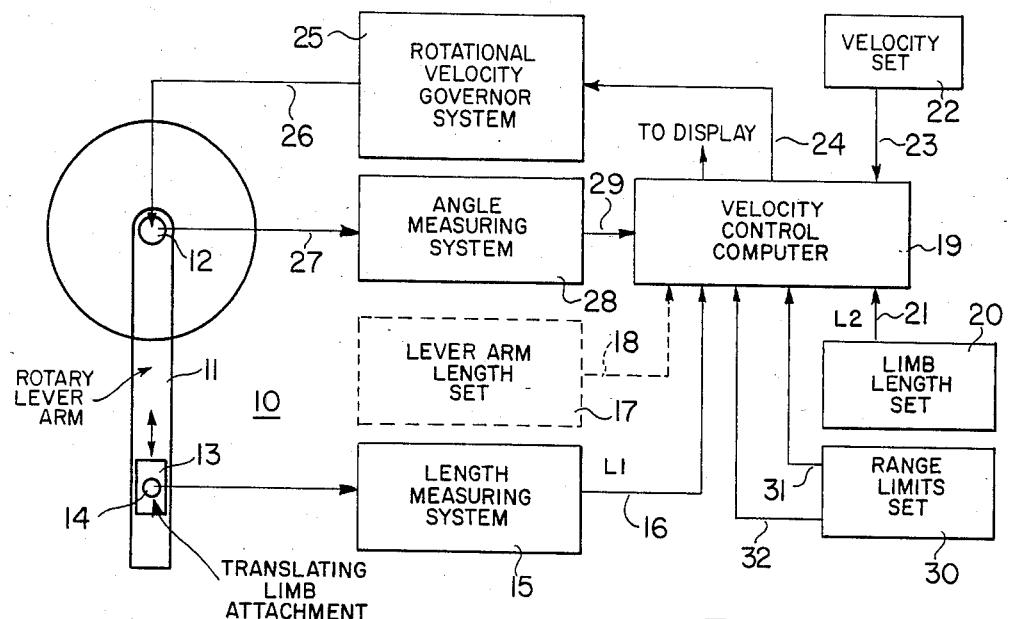
FIG. 1
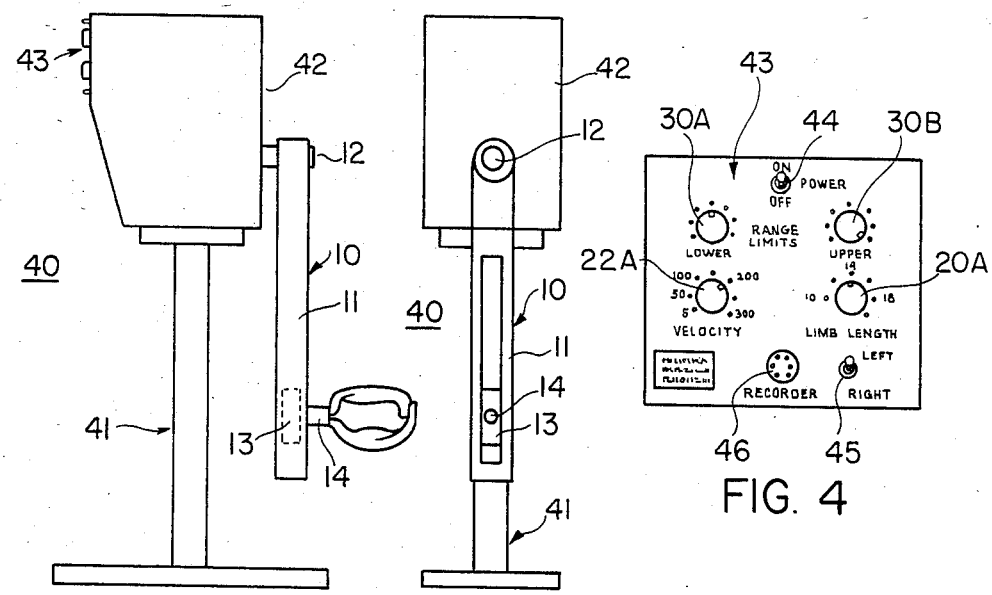
FIG. 2
FIG. 3
FIG. 4

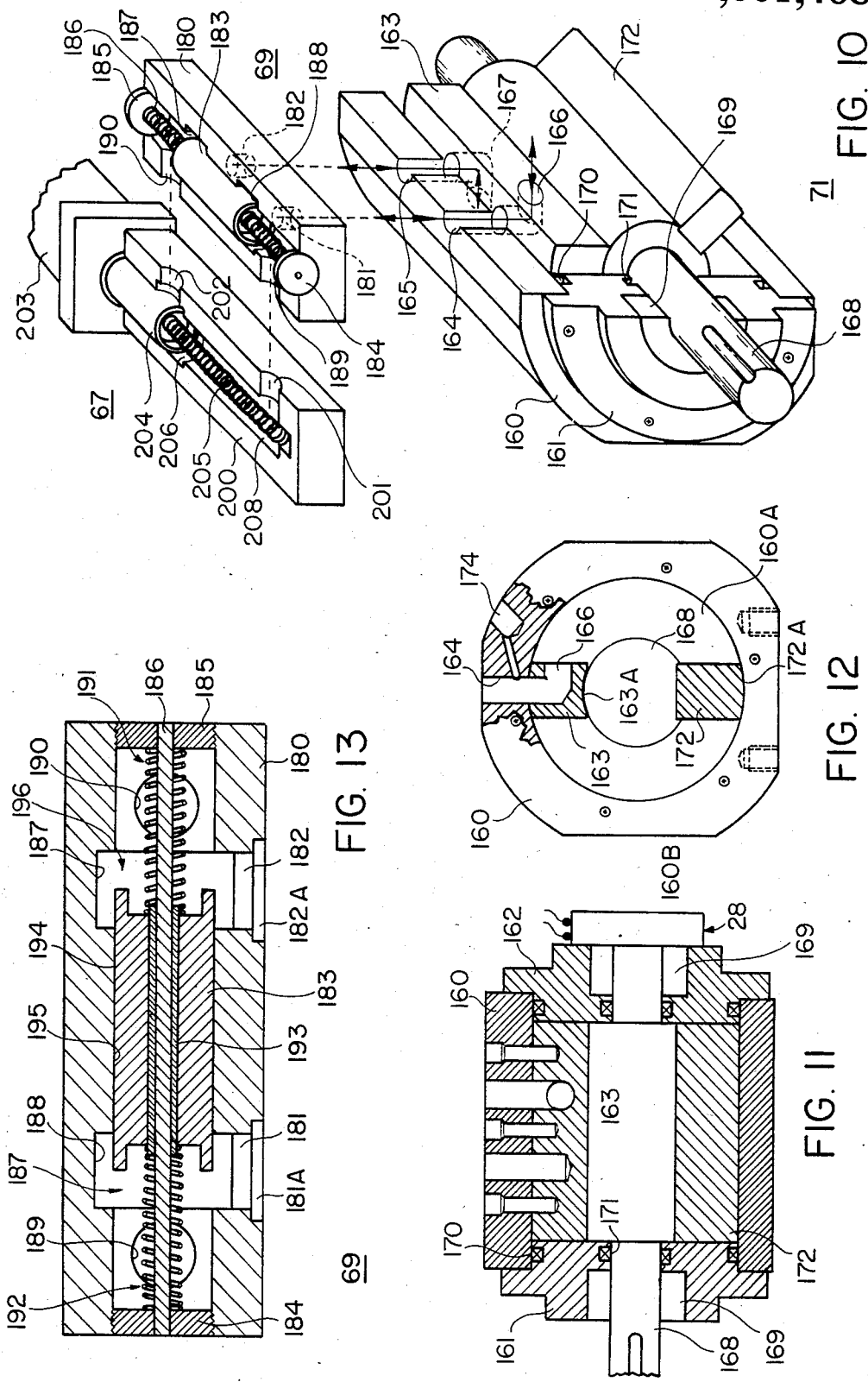

EXERCISE AND DIAGNOSTIC SYSTEM AND METHOD

This invention relates generally to exercise systems and methods and, more specifically, to exercise and diagnostic systems and methods which permit evaluation and improvement of the performance of the human skeletal and musculature systems in both training and rehabilitation situations.

Research conducted over the past decade has demonstrated the value of isokinetic exercise from the standpoint of rehabilitating injured human joints and associated muscle groups as well as training joints and muscle groups for improvement of human performance. The term "isokinetic" refers to the exercise concept that involves restricting the movement of a portion of the body about a particular anatomical axis of rotation to a constant rotational velocity. This is achieved by applying an accomodating resistance to the contracting muscle, that is a constantly varying resistive force. This resistive force changes in value throughout the range of motion of the limb in a manner which mimics the varying amount of force that the associated muscle group is able to generate at various points throughout the contraction.

The observation that the amount of force which a muscle group generates varies throughout the range of motiton of the associated joint may be explained in terms of anatomical axis of rotation (i.e., a variable biological lever length advantage), enzymatic profile (i.e., intercellular contractile and metabolic protein composition), and ballistic considerations. An example of this phenomenon can be shown in the knee joint extension during which the quadriceps muscle is seen to develop peak torque at about sixty degrees of rotation.

Conventional methods of "free weights" exercise require the muscle to act against a load which cannot be greater than the least torque developed at the weakest point in the range of motion of the joint. Thus, with free weights the muscle operates at a reasonable work load in only a small portion of the overall range of motion and does not experience optimal loading during the stronger points in the range of motion.

Semi-accomodating resistance exercise such as is provided in some cam-based exercise systems, wherein the load on the muscle is biased and semi-variable, are at best approximations to the variations in force generated by the particular muscle groups sampled from a cross-section of individuals. This approximation of variable force generation, which may be visualized as a quasi-bell shaped curve of force plotted against degrees of range of motion, is used to shape a cam to control application of the resistive force in a semi-accomodating, variable manner.

Isokinetic exercise systems, on the other hand, provide completely accomodating resistance which offers a variable force opposing muscle contraction in a manner which imitates the variable force generated by the involved muscle group. In this type of system, the rotational velocity of the lever arm to which the human limb is attached is constrained to a maximum permitted value and any force exerted by the limb which tends to accelerate the lever arm beyond that maximum value is matched with an accomodating resistance. Accordingly, the muscle group involved may operate at its optimal tension development throughout the entire range of motion. The net rehabilitation benefit or the net gain in human performance in a training modality is substantially greater than that achieved with conventional exercise modes.

The greater benefits of isokinetic exercise can also be explained in terms of the effect on the recruitment pattern of specific muscle fiber types. It has been established that skeletal muscle is an admixture of two distinct cell types. One type of cell is relatively large and rich in anaerobic enzymes which carry on the cell's metabolic need without oxygen. The other cells are smaller and rich in aerobic components which rely on the presence of oxygen to supply the cell's metabolic requirements. Research has shown that, at large loads and low speeds of contraction, the muscle cell type primarily involved in the exercise is the anaerobic, large diameter cell. Conversely, at low loads and high speed of contraction, the aerobic, smaller diameter cells are primarily involved.

A rehabilitation program which imposes a work load on the muscle groups at either of the extremes of load and velocity will be neurally recruiting one particular muscle cell type. Therefore, it is essential that the muscle be exercised at the center of the force-velocity curve for maximum rehabilitation benefit. This can best be achieved with isokinetic exercise and specific speed selection for the constant contractile velocity of the involved muscle group.

Isokinetic exercise systems of the prior art (for example, the system shown in Perrine U.S. Pat. No. 3,465,592) involve a fixed length of lever arm which is attempted to be adjusted accurately to the length of the limb being exercised by aligning as closely as possible the anatomical axis of rotation with the fixed machine axis of rotation. However, this alignment can only be approximated prior to the onset of exercise and hence the rotational velocity of the limb will differ from the rotational velocity of the lever arm.

Moreover, a further complicating factor is that the axis of rotation of a human joint is dynamic and shifts during the exercise motion. Even if the position of the involved joint is mechanically constrained, the anatomical axis of rotation will shift during the exercise motion. As a result the constraining of the fixed length lever arm to a maximum permitted angular velocity means that the angular velocity of the involved limb about the anatomical axis of rotation will vary.

An additional disadvantage of the fixed length lever arm systems of the prior art is that substantial joint compression is introduced by constraining the human limb to a fixed path of rotation at the point of attachment to the lever arm. This joint compression produces an uncomfortable level of pain in certain individuals with joint problems. More seriously, the magnitude of joint compression produced in prior art systems precludes early initiation of rehabilitative exercise in patients which have undergone surgery on the involved joint.

A further disadvantage of the fixed length lever arm systems of the prior art is that the ability to isolate muscle groups involved in extension and flexion is substantially reduced and it is observed that substantial motion of other portions of the body are involved during the exercise motion. The unnatural feeling of the exercise motion is a deterrent to patient interest and willingness to follow the exercise regimen over the period of rehabilitation.

Accordingly, it is the principal object of this invention to provide an improved exercise system and method.

It is another object of this invention to provide an isokinetic exercise system and method which enables closer achievement of true isokinetic joint rotation velocity.

It is another object of this invention to provide an exercise system and method which substantially reduces joint compression and provides improved muscle group isolation during the exercise motion.

It is another object of this invention to provide an exercise system and method which is easier to set up and operate and provides more accurate diagnostic information.

One aspect of this invention features a muscle exercise and diagnostic system which includes a lever arm and an arrangement for mounting the lever arm for rotation about a fixed axis. A connecting arrangement is provided for connecting a selected portion of the human body to the lever arm for rotation with the lever arm about a selected anatomical axis of rotation. The connecting arrangement includes a mounting arrangement establishing a fixed tangential mounting relation and a sliding radial mounting relation between the lever arm and the body portion. The system further includes a velocity control arrangement operatively associated with the lever arm for limiting the maximum permitted instantaneous rotational velocity of the lever arm to a value predetermined in accordance with a preselected velocity control function which includes measured values of the distances from the point of attachment to the anatomical axis and to the fixed axis.

In a preferred embodiment, the mounting arrangement provides a fixed connection to the body portion and a radially sliding connection to the lever arm. In a simplified version of the invention, the anatomical and machine lever arm distances may be measured once and input as fixed values to to the velocity control arrangement, ignoring the changes which will occur during the exercise motion in the machine lever arm distance. A preferred embodiment incorporates a machine lever length tracking arrangement associated with the mounting arrangement for registering the distance from the connection point to the fixed axis and supplying the registered distance value to the velocity control arrangement, and a manual control for inputting to the velocity control arrangement a measured value of the distance from the fixed connection to the anatomical axis. In this manner the maximum permitted angular velocity of the lever arm will be adjusted to take into account the changes in lever arm length during the exercise motion.

A preferred embodiment of the exercise system of this invention also features an arrangement for automatically limiting the range of motion of the lever arm to a preset maximum angle or to both preset maximum (upper) and minimum (lower) angles. In addition, an acceleration limiting function to provide resistance to unfettered acceleration during initial movement of the lever arm is provided.

The invention also features an improved hydraulic actuator and valve based system for achieving the rotational velocity governing function coupled with a tight servo control loop, including tracking of the position of the proportional control valve in an inner servo loop and tracking of the actual angular velocity as a part of an outer servo control loop in the special purpose analog computer version of the invention. The basic control functions involved in the velocity control computer arrangement can also be readily achieved in a microprocessor real time control system embodiment which also offers enhanced data aquisition and data computing capability.

This invention also features a method for controlled accomodating resistance exercise which includes the steps of mounting a lever arm for rotation about a fixed axis and disposing a human body attachment device on the lever arm in a tangentially fixed and radially movable mounting relation. The method further involves the steps of contacting the attachment device with a selected portion of the human body for rotation of the attachment device and lever arm with the body portion about an anatomical axis of rotation, measuring the lever arm radius from the attachment device to the fixed axis of rotation, measuring the anatomical radius from the attachment device to the anatomical axis of rotation, and restraining rotation of the lever arm to an angular velocity less than or equal to an value predetermined in accordance with a preselected velocity control function which includes the measured lever arm radius and the measured anatomical radius.

Preferably the step of measuring the lever arm radius comprises constantly monitoring the lever arm radius value as the body portion traverses a rotational exercise path; and the step of restraining rotation of the lever arm is performed in accordance with a time-varying velocity control function which includes the time-varying lever arm radius. To achieve isokinetic rotation of the body portion, the preselected velocity control function is prearranged to provide a substantially constant maximum angular velocity of rotation of the body portion about the anatomical axis of rotation. Other velocity control functions which vary the permitted maximum angular velocity of rotation about the anatomical axis of rotation may be provided. For example, the velocity control function may involve limiting the initial acceleration of the lever arm by providing a ramp up function of permitted maximum angular velocity so that the body portion experiences a resistive force earlier in the exercise motion.

The various features of this invention provide significant improvements in accomodating resistance exercise systems. Joint compression is substantially alleviated by the connection arrangement to the human body permitting radial motion during the exercise motion. This permitted radial motion together with the compensation for maximum permitted angular velocity which is achieved in the velocity computer arrangement based on the measured length of the lever arm and the measured length of the human lever (i.e., from the point of attachment to the anatomical axis of rotation) greatly facilitates patient set-up on the system and produces more accurate velocity control in terms of the actual rotational velocity of the human joint. It is not necessary to attempt to precisely align the anatomical axis with the lever arm axis, and variations up to two or three inches will produce accurate results.

By permitting the length of the lever arm to vary during the exercise motion and compensating for such motion in the velocity control computer the change in position of the anatomical axis of rotation during the exercise motion does not affect the accuracy of velocity control. Moreover, the exercise motion is more natural to the patient or athlete. In the diagnostic situation, where isolation of muscle groups for measurement of strength (e.g. peak torque developed at certain speeds) is desired, the system and method of this invention provide improved isolation of muscle group activity during flexion and extension of the limb.

The feature of computer control of velocity permits a number of new features to be included in the accomodating resistance exercise system. Computer controlled limits on the angular excursion of the lever arm permit the system to limit the range of motion of the joint with a soft stopping action to avoid jarring the limb. This enables the system to be used in a post-operation situation where the patient's range of motion of the affected joint must be limited without requiring the attendance of the therapist to restrain the patient's movements with his hands.

The velocity control computer provides controlled initial acceleration of the lever arm so that resistance is felt early in the movement of the limb and builds up slowly to avoid the sudden loading effect that is present in certain prior art systems. The various servo control loops in the velocity computer system and the driving circuitry for the hydraulic system components provide more accurate velocity control. Furthermore, the introduction of the linearizer feature provides accurate velocity setting and regulation across the entire velocity range of the system.

The use of a velocity control computer in the form of a software program controlled microcomputer system will provide new flexibility in velocity and range of motion control as well as providing built in data storage and management capability. With this type of system, researchers can experiment with different anatomical demand velocity functions throughout the exercise motion. For example, instead of a constant speed contraction of muscle groups, the system could impress a sine wave variation on permitted velocity, either increasing or decreasing the permitted velocity in the mid-range of the exercise motion.

Other objects, features and advantages of this invention will be apparent from the detailed description of several embodiments set forth below in conjunction with the accompanying drawings.

FIG. 1 is a general block schematic diagram of an exercise system in accordance with this invention.

FIGS. 2 and 3 are elevational views of one version of the mechanical system package of one embodiment of this invention.

FIG. 4 is a pictorial diagram of a control panel useful in one embodiment of this invention.

FIGS. 10–13 illustrate the mechanical and operational aspects of the hydraulic elements of a preferred form of velocity governor system in accordance with this invention.

FIG. 14 illustrates an alternative embodiment of a velocity control computer in accordance with this invention.

Figure 5:
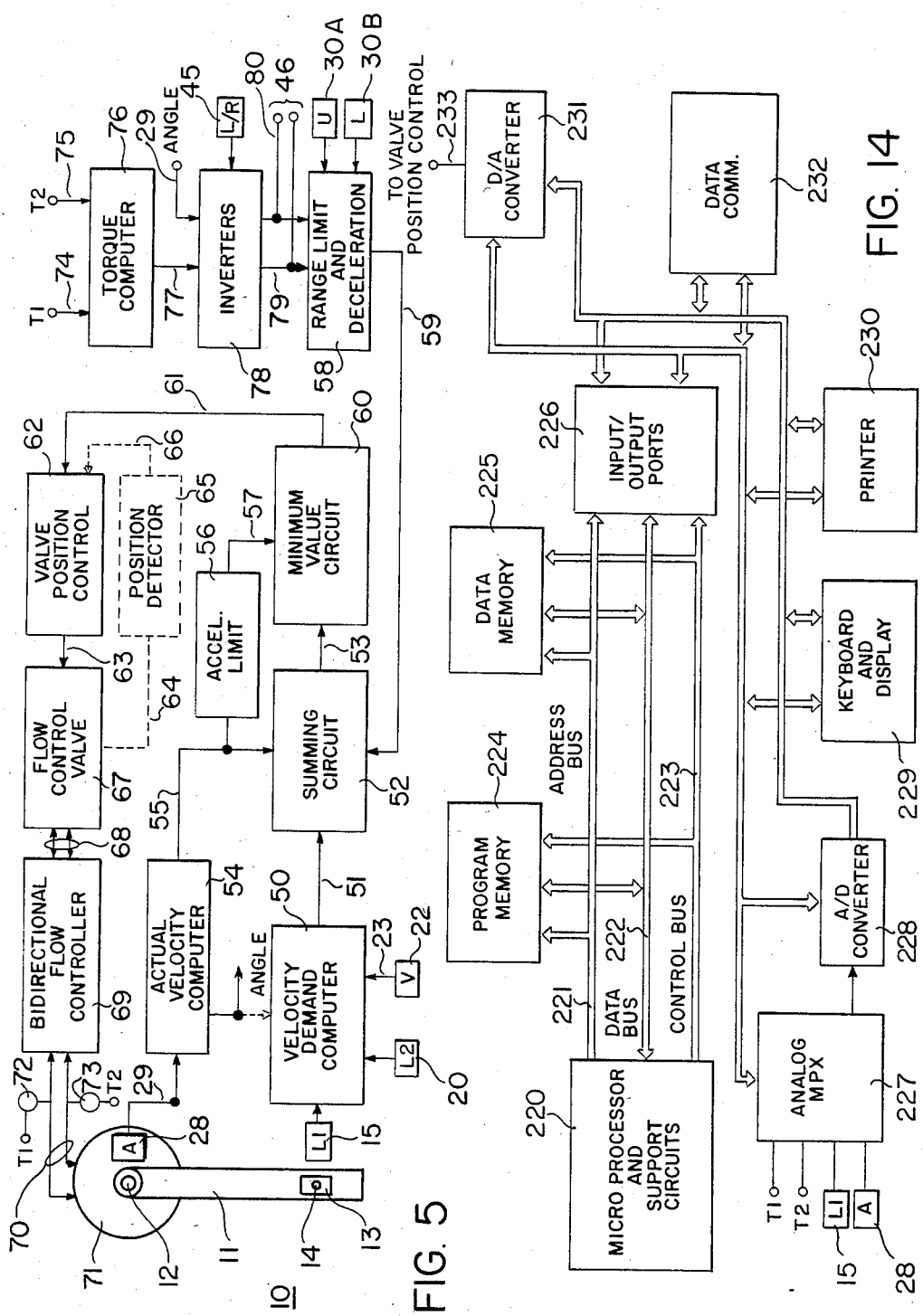
FIG. 5 is a block diagram of one embodiment of the system of this invention implemented in analog computer circuit form.

FIG. 1 shows in schematic form the elements of a muscle exercise and diagnostic system in accordance with this invention. Lever arm assembly 10 includes a lever arm 11 which is mounted on a shaft 12 for rotation about the axis of the shaft. The shaft 12 is fixed in space by a stand or support arrangement such as is shown schematically in FIG. 2. Connecting arrangement 13 provides means for connecting a portion of the human body to lever arm 11 using a convenient connection attachment 14 such as the ankle cuff shown in FIG. 2. Other forms of attachment can be provided for other limbs and body parts. Connection arrangement 13 is mounted to lever arm 11 utilizing a mounting arrangement which provides a sliding radial mounting relation, but a fixed tangential mounting relation. This may be accomplished for example by utilizing a carriage arrangement mounted on wheel bearings and traversing a channel within a hollow rectangular arm. Numerous different mechanical assemblies could be employed to achieve this mounting relationship.

A length measuring system 15 is operatively associated with the translating limb attachment arrangement 13 to continuously monitor the distance from the point of attachment of the human body to the axis of the shaft 12 during the exercise motion. This length measuring system may comprise a potentiometer operatively connected to the attachment arrangement 13 to register the length as a proportional resistance. A pulley and belt arrangement connected to a carriage assembly is a presently preferred method for interfacing to a rotary potentiometer to provide this length monitoring function. The output signal 16 from the length measuring system 15 is coupled into a velocity control computer 19 whose function will be described below.

An angle measuring system 28 is appropriately coupled to shaft 12 via some mechanical linkage signified by the line 27 to continuously monitor the angle of the lever arm 11. This function can be readily performed by a rotary potentiometer attached to the shaft 12. The output signal 29 from the angle measuring system is also coupled into the velocity control computer 19.

Velocity control computer 19 also receives a limb length input signal 21 from a limb length set control 20, a velocity set input signal from a velocity set control 22, and range limits signals 31 and 32 from a range limits setting control 30. The lever arm length set signal 18 from setting control 17 is used in an optional embodiment and will be described below. Velocity control computer 19 utilizes all of the active input signals to produce an output velocity control signal 24 for controlling a rotational velocity governor system 25 and thereby establishing a maximum permitted angular velocity of the lever arm 11. As will be discussed later, there are a number of simple and complex functions which may be utilized by the velocity control computer 19 in determining the velocity control signal 24.

The essential fuction of the velocity control computer is to utilize the lever arm length signal 16 and the limb length set signal 21 to adjust the velocity control signal 24 to compensate for differences between the lever arm length and the limb length, that is, differences due to permitted misalignment of the fixed axis of rotation of lever arm 11 and the anatomical axis of rotation of the limb or other body part attached to the lever arm. The continuous monitoring of the lever arm length enables the velocity control computer to continuously adjust the velocity control signal as the lever arm length changes during the exercise motion due to dynamic changes in the position of the anatomical axis of rotation.

It can be shown that, in the case where an isokinetic velocity of rotation of the human limb about the anatomical axis is desired, the velocity control computer 19 may ratio the monitored lever arm length signal L1 with the measured limb length signal L2 and multiply the ratio by the velocity set value to obtain a velocity control signal which will provide a maximum permitted angular velocity of the lever arm which correspondingly produces a maximum permitted angular velocity of the limb which is closely approximated to the velocity set value. Other factors enter into the velocity correction function, but they are secondary factors, such as translational velocity of the attachment during the exercise motion, which are small and can be ignored.

It will be appreciated that, as the exercise motion progresses and the anatomical axis shifts, the lever arm distance will change and the velocity control computer will compensate by changing the maximum permitted lever arm velocity to keep the maximum human limb velocity constant. This contrasts with the fixed path lever arm systems of the prior art in which the lever arm rotational velocity is maintained at a fixed maximum permitted value so the rotational velocity of the human limb is necessarily changing during the exercise motion.

The velocity control computer 19 preferably utilizes the angle input 29 as part of a servo control loop to maintain good regulation on the velocity control signal. It may also use the angle input signal 29 together with the range limits signals 31 and 32 to control the permitted range of motion of the lever arm. The manner of accomplishment of this function depends on the type of velocity control computer utilized in the system. In an analog computer version, a signal indicating the direction of the motion of the arm may be required and this can be derived in one of the embodiments of the invention described below from a torque signal which has different polarity for different directions of motion.

It should be understood that, since this invention utilizes computer circuitry to derive the velocity control signal, other anatomical velocity functions than the isokinetic function could be programmed into the system. For example, the maximum permitted anatomical velocity function could be a sine wave or have some other arbitrary shape of permitted velocity versus angle over the range of exercise motion.

The rotational velocity governor system 25 may comprise a number of different hydraulic, motor and gear train, and motor and clutch arrangements which permit electrical control of the permitted maximum rtational velocity of the lever arm 11. A preferred form of hydraulic actuator and proportional control valve arrangement for accomplishing this function in accordance with this invention is described below.

FIGS. 2 and 3 illustrate schematically one approach to packaging the components of this invention in an integrated exercise system 40. The system 40 includes a stand arrangement which supports the lever arm assembly 10 mounted on a shaft 12 which extends into housing 42. Internally mounted in the housing 42 is the hydraulic actuator and valve system which is depicted in FIGS. 10-14. A circuit board containing the components of the velocity control computer is also mounted within the housing 42, and the various settings used by the velocity control computer are provided on the control panel 43 which is depicted in detail in FIG. 4.

It is generally preferrable that the stand arrangement 41 be integrated into a mounting arrangement with a chair and/or bed arrangement with good mounting stability. A number of various types of mounting arrangements can be employed along with a number of arrangements for positioning the patient or athlete using the system with respect to the lever arm. A variety of different lever arms and other attachments may be provided to adapt the system for use with any of the joints of the human body. for this purpose it is preferable that the lever arm be attached to the shaft in a manner which provides an easy connect/disconnect function and that the signal lines to the potentiometer in the lever arm be coupled through an externally accessible electrical connector.

In setting up the system for use by a patient, for example for exercise of the knee, the patient will be seated in a chair to which the stand 41 is preferably rigidly attached and the patients ankle will be strapped to the lever arm using the cuff arrangement shown in FIG. 2. The patient's knee will be placed in the approximate vicinity of the axis of rotation of the shaft 12, but it is only necessary to avoid a displacement of less than about three inches between the fixed system axis and the anatomical axis. The length of the patient's limb from joint to the attachment point of the cuff is measured and dialed in on the control 20A on the control panel 43. The switch for right or left leg is appropriately positioned, and the desired isokinetic velocity for the patient's limb is set on the control 22A. if range limits are desired, they are set on the controls 30A and 30B. The system is then prepared for the particular exercise bout prescribed for the patient. A strip chart recorder may be attached to the system to record the angular range of exercise motion and the torque developed by the patient during the exercise motion. (The circuitry for developing these signals is described below.)

FIG. 5 illustrates in more detail the elements of a preferred embodiment of ths invention in which the velocity control computer is implemented in a special purpose analog computer form and the velocity governor system is implemented in the form of a hydraulic system comprising a rotary actuator 71, a bidirectional flow control valve system 69, and a valve position control system 67 which may be a solenoid actuated servo valve.

As shown in FIG. 5, the velocity control computer in this analog embodiment includes a velocity demand computer 50, an actual velocity computer 54, a range limit and deceleration computer 58, a summing circuit 52, an acceleration limit circuit 56, a minimum value circuit 60, and a valve position control circuit 62. Depending on the type of valve position control circuit utilized and the flow control valve utilized, an inner servo loop involving the position detection circuit 65 may be employed to maintain control of the position of the flow control valve element. As will be seen from the detailed description of an actual embodiment of this analog version of the invention, the velocity control function also involves an outer servo loop comprising the actual velocity computer and the velocity demand computer whose outputs are summed in opposite polarity in summing circuit 52 to develop a form of error signal which is then summed with the position detection signal output of position detector 65 to develop the final error signal which is used to correct the position of the solenoid control valve.

In addition the bidirectional flow controller 69 together with the flow control valve 67 comprises a form of hydraulic servo system which further assists in maintaining regulation of the maximum permitted rotational velocity by regulating the hydraulic flow in accordance with the back pressure built up behind the controlled orfice in the proportional control valve as the torque on the rotating vane of the actuator is increased.

The acceleration limit circuit 56 takes over control of the maximum permitted rotational velocity during initial acceleration of the lever arm so that the permitted velocity will ramp up to the final value determined by the velocity demand computer. The range limit and deceleration circuit similarly takes over control of the velocity control signal when an angular limit is reached and controlled deceleration to a stop is produced until torque reversal is sensed.

The torque computer 76 computes the value and sign of the applied torque from the oppositely poled pressure transducers 72 and 73 connected to the bidirectional flow lines in the hydraulic circuit. The angle and torque signals on lines 77 and 29 are fed through selective inverter circuits controlled by the left/right switch 45 (FIG. 4) so that the signal polarity will be correct regardless of whether the system is being used for left or right leg exercise.

In FIG. 5 the angle output from the actual velocity computer circuit 54 is shown as optionally being coupled into the velocity demand computer 50. This shows that it may in some instances be desired to have the demand velocity signal take on different values as a function of the angle of the lever arm during the range of exercise motion. It may also be desirable or necessary, in some instances, to couple the upper and lower range limit signals into the velocity demand computer to assist in setting up an anatomical velocity demand signal which is a function of lever arm angle.

Figure 6:
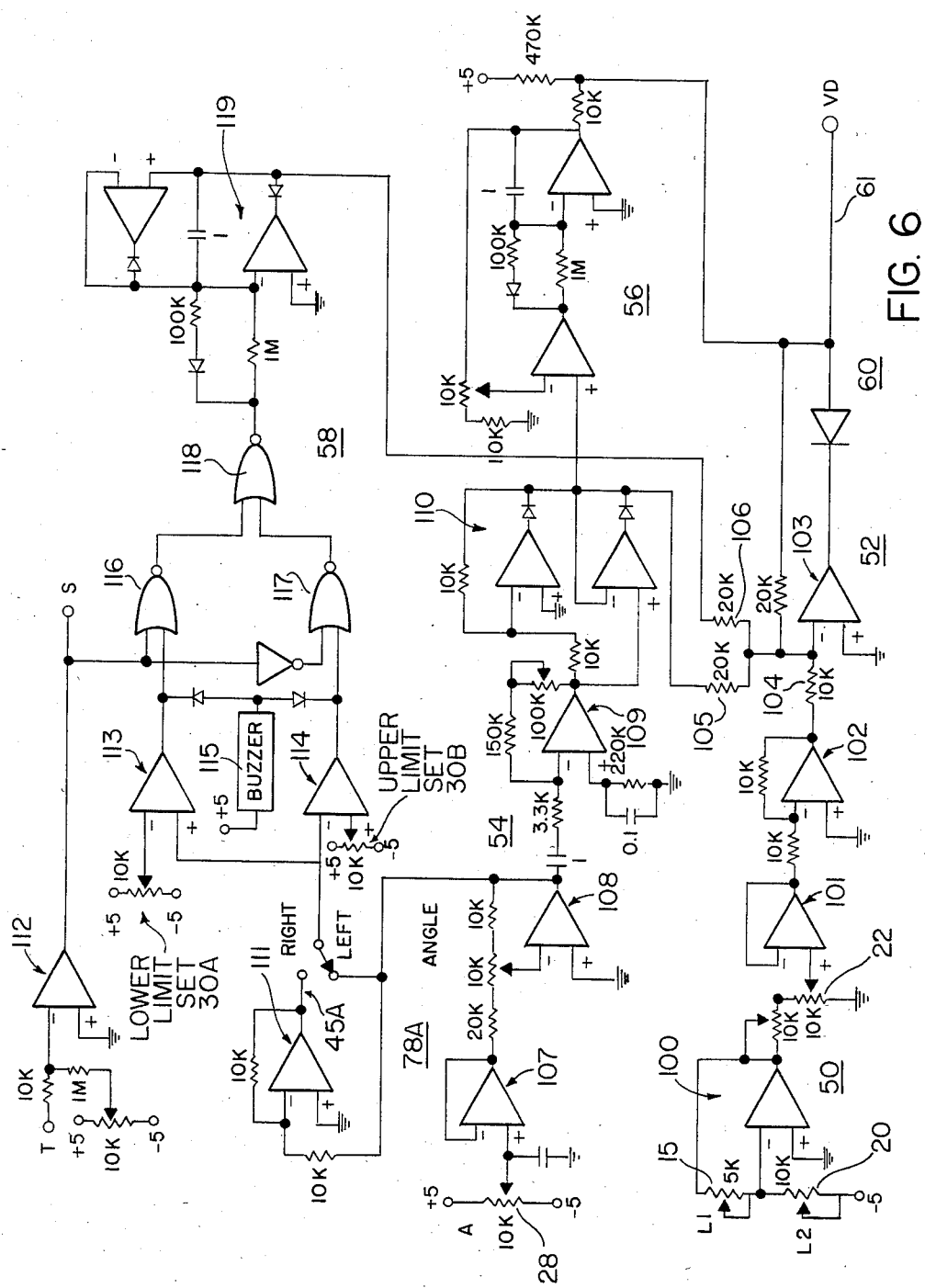
FIGS. 6–9 are detailed schematic diagrams showing the structure and operation of one embodiment of the system of this invention in an analog computer form.

FIG. 6 shows the actual circuitry of a preferred embodiment of an analog version of this invention. In this embodiment the velocity demand computer 50 includes ratio circuit 100 which produces and output signal corrsponding to the ratio L1/L2. This ratio signal is proportioned in the potentiometer 22 which is the anatomical demand velocity setting from the control panel. The proportioned output is an analog signal representation of the function VD=VA(L1/L2), where VA is the anatomical demand velocity and VD is the corresponding demand velocity for the lever arm system. This signal is inverted by the circuits 101 and 102 before being fed to the summing circuit 52.

The actual velocity computer 54 includes circuit arrangements 107 and 108 which buffer and invert the signal from the angle potentiometer 28 and couple the resultant signal to a differentiation circuit arrangement 109 which computes the velocity as a rate of change of angle. The output signal from the differentiation circuit 109 is coupled into absolute value circuit 110 to produce an analog signal of single polarity whose magnitude is proportional to the absolute velocity of the lever arm. This absolute actual velocity signal Va is coupled to the analog summing circuit 103. The demand and actual velocity signals are arranged to be of opposite polarity so that the summing circuit is actually subtracting the values of the two signals. In addition it should be noted that the demand velocity signal is coupled into the summing circuit through a 10K resistor 104 and the actual velocity signal is coupled into the summing circuit through a 20K resistor. Accordingly, the output of the summing circuit is, neglecting other inputs, 2VD−Va.

The acceleration limiting circuit 56 is a non-linear filter circuit whose input/output characteristic is such that the output value is 1.2 times the value of the input absolute velocity signal. However, the filter also has a characteristic that its output cannot change faster than a predefined rate. The output is also slightly offset to be non-zero under all conditions. This output is applied to the minimum value circuit 60 and thus the final velocity command signal is the minimum of the output of the summing circuit and the output of this acceleration limit circuit. The acceleration limit circuit thus controls the permitted rate of acceleration of the lever arm during the initial acceleration up to the final demand velocity.

The range limit and deceleration circuit 58 also has its output summed in the summing circuit 52 and functions to provide a controlled deceleration when preset angular limits of exercise motion have been reached. The angle signal output from actual velocity computer 54 is coupled into a pair of comparator circuits 113 and 114 with either direct coupling or through an inverter circuit 111, depending on the setting of the right/left switch 45A. The other inputs to the comparator circuits 113 and 114 are the lower limit set value and the upper limit set value. The outputs of the comparator circuits 113 and 114 are coupled as inputs to NOR logic gates 116 and 117, respectively. The other logic input to NOR gate 116 is the output of comparator circuit 112 which has a logic signal output which is a function of the sign of the torque signal T which is produced in the circuit of FIG. 8. The other logic input to NOR gate 117 is the logically inverted output of comparator circuit 112. The outputs of NOR gates 116 and 117 are coupled as inputs to NOR gate 118. The output of NOR gate 118 controls an integrator circuit 119 such that when gate 118 has a logic LOW output, integrator circuit 119 produces a braking signal voltage which is summed in the summing circuit 52 and has the characteristic that it drives the output of the summing circuit toward a command velocity value corresponding to zero velocity. This is accomplished in a sufficiently controlled and gradual manner that the lever arm of the system is brought to a gradual stop. When the person using the system reverses the torque on the lever arm, the integrator circuit 119 is rapidly reset as the logic value output of the NOR gate 118 goes HIGH. This permits acceleration of the lever arm in the opposite direction under the control of the acceleration limit circuit 56.

Figures 7, 8:
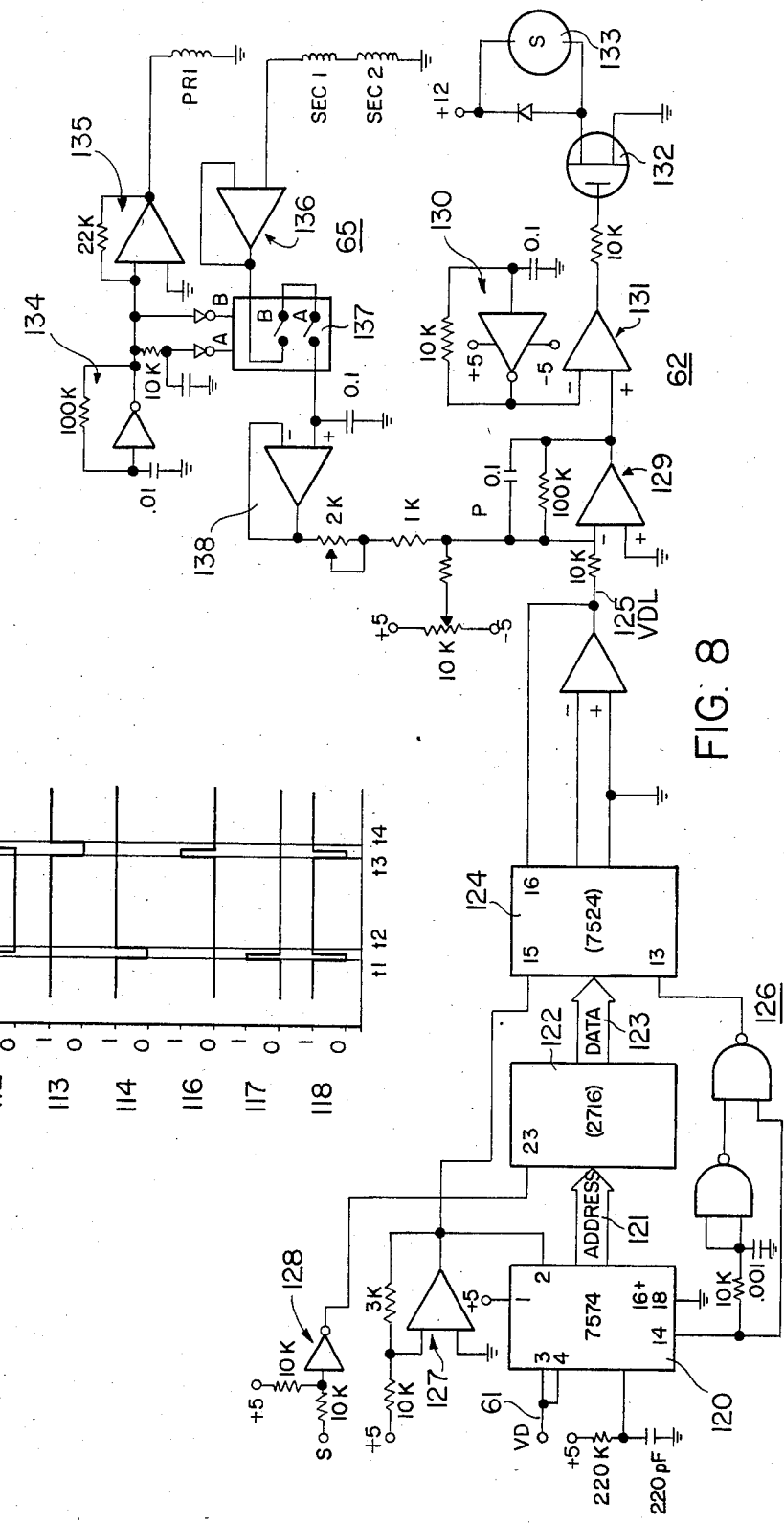
Figure 9:
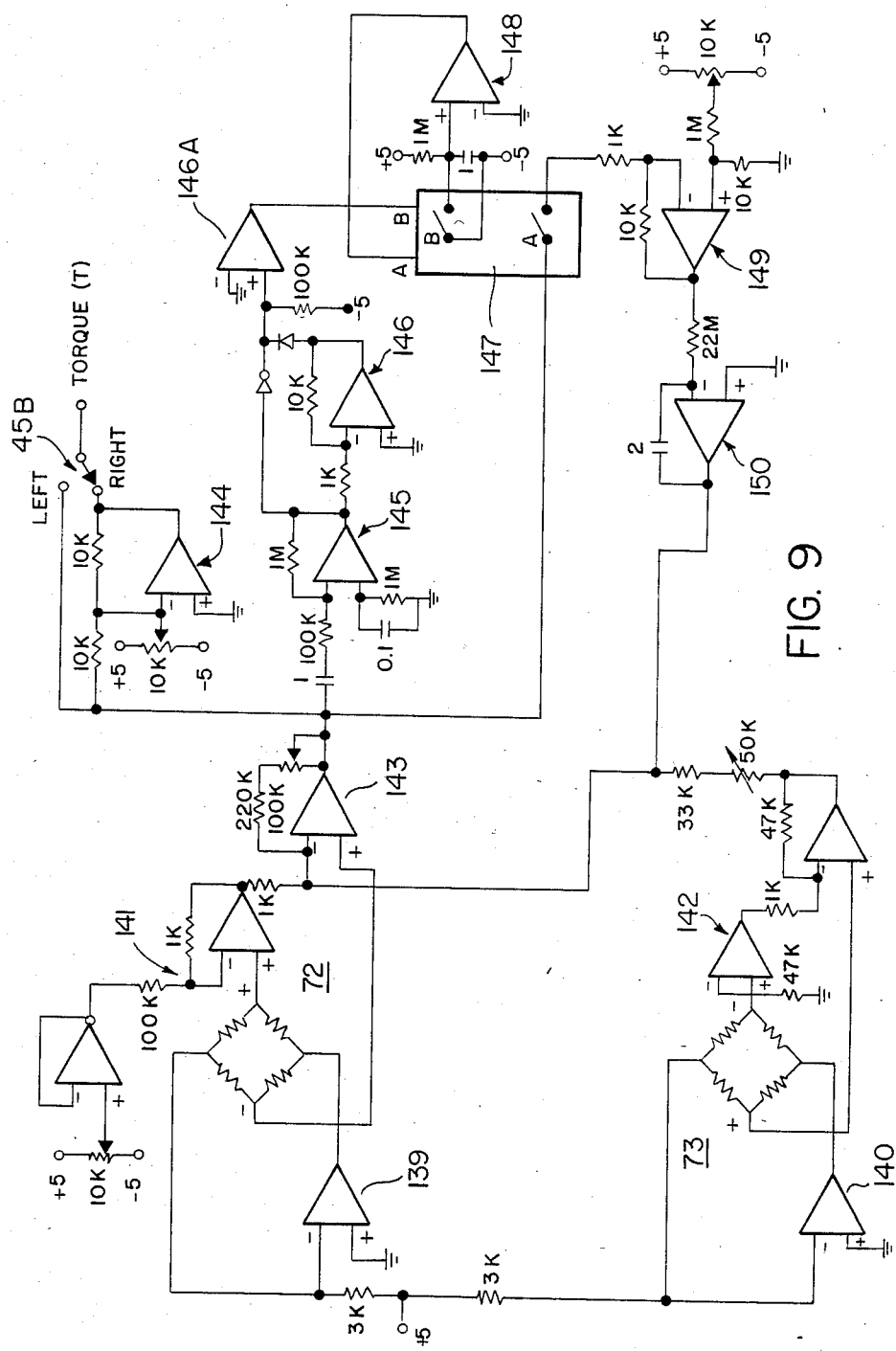

FIG. 7 shows the operation of the comparators 112, 113, and 114 in a typical operation sequence. Prior to time t1, the lever arm is moving in a positive direction so that the ANGLE signal is going positive toward the upper limit setting U. Since the torque is in a positive direction, the output of comparator 112 is a logic HIGH value (designated a 1 on the graph). Since the ANGLE signal value exceeds the lower limit setting L, the output of comparator 113 is at a logic HIGH value. Furthermore, since the ANGLE signal value is less than the upper limit setting U, the output of the comparator 114 is also at a logic HIGH value. Note that the ANGLE signal is coupled to the minus input of comparator 114 and to the plus input of comparator 113. Thus the output of comparator 114 is HIGH when the ANGLE signal is less than the upper limit setting U whereas the output of the comparator 113 is HIGH when the ANGLE signal is greater than the lower limit setting L.

During the time period prior to t1, the logic HIGH value of the outputs of comparators 112 and 113 causes the output of NOR gate 116 to be LOW. The output of NOR gate 117 is LOW because the output of comparator 114 is HIGH. NOR gates 116 and 117 will have logic HIGH outputs only when both of their inputs are at a logic LOW level. Similarly, NOR gate 118 will have a logic HIGH output only when both of its inputs are at a logic LOW level. Since both signal inputs to NOR gate 118 are LOW during the period prior to time t1, the output of NOR gate 118 is HIGH and the integrator circuit 119 is held in a reset condition so that its signal output has no affect on the velocity command signal.

At time t1, the angle signal A reaches the upper limit setting U so the output of comparator 114 goes LOW. Thus, at time t1, both inputs to NOR gate 117 are LOW and its output goes HIGH. As the output of NOR gate 117 goes HIGH, the output of NOR gate 118 goes LOW, triggering the integrator circuit 199 to provide the braking signal to summing circuit 52. Also, when the output of comparator 114 goes LOW at time t1, the buzzer 115 sounds. The combination of hearing the buzzer and feeling the braking force on the lever arm will cause the patient to stop exerting positive torque on the lever arm and shortly thereafter to begin to exert negative torque to move the lever arm in the opposite direction. Thus, shortly after time t1, the torque signal reversal causes the output of comparator 112 to go LOW. The inversion of this LOW output to a HIGH input to NOR gate 117 causes NOR gate 117 to go to a LOW input again. The output of NOR gate 116 remains LOW because the output of comparator 113 is still HIGH. Accordingly, as NOR gate 117 goes LOW, NOR gate 118 goes HIGH and resets the integrator circuit 119 to release the braking signal and permit the lever arm to be accelerated in the other direction until the maximum permitted velocity is reached.

At time t2, angle signal has declined below the upper limit set value U and the output of comparator 114 goes HIGH again, but this does not change the output of NOR gate 117 since its other input is already HIGH to force the output LOW. During the period from t2 to t3 the outputs of NOR gate 116 and 117 remain LOW and thus the output of NOR gate 118 remains HIGH, keeping the integrator circuit 119 in a reset condition.

At time t3 the angle signal reaches the value of the lower limit set, and the output of comparator 113 goes LOW. Since the output of comparator 112 is already LOW, both inputs to NOR gate 116 are LOW and its output goes HIGH. This forces the output of NOR gate 118 LOW at time t3, and triggers the integrator circuit 119 to apply the braking signal once again. The buzzer again sounds and the patient will stop applying negative torque and begin applying positive torque to the lever arm a short time after time t3. When the torque goes positive, the output of comparator 112 goes HIGH, and this causes the output of NOR gate 116 to go LOW again and, in turn, the output of NOR gate 118 to go HIGH again. When NOR gate 118 goes HIGH, integrator circuit 119 is reset again to release the braking signal and to permit the lever arm to be accelerated in the positive direction.

At time t4, the output of comparator 113 goes HIGH again as the value of the angle signal increases above the lower limit set value again, but no other action of consequence occurs at this time. After time t4, the circuitry is in the same state as prior to time t1, and the operating cycle repeats until the patient discontinues the exercise activity.

It should be noted at this time that the purpose of the left/right switch 45 is to condition the polarities of the angle and torque signals relative to the upper and lower limit setting on the angle so that the logic circuitry of the angle limit and deceleration circuit will function in the proper manner for exercise of either right or left limbs of the body. In addition the left/right switch controls the selective inversion of the angle and torque signals which may be coupled into a chart recorder so that the angle and torque readings recorded will always be in the same direction on the chart regardless of which limb is being exercised on the system. In other words, during exercise of the knee, for example, the torque developed by the hamstring muscle group during flexion of the knee (lowering of the lever arm) will always be recorded to the left of the baseline of the chart and the torque developed by the quadriceps during extension of the knee will always be recorded to the right of baseline regardless of whether the left or right leg is involved. Similarly, the range of motion of the joint during flexion and extension will always appear on the chart to the left and right of the baseline, respectively, regardless of which leg is being exercised. This assists in interpretation of the charts developed on the recorder.

It should be understood that the left/right switch controlling signal polarity for angle and torque is for convenience only and could be eliminated provided the limit settings on range of motion were understood to be reversed during exercise of one side of the body verses the other and that the torque and angle graphs on the chart recorder are reversed in a similar manner. It should also be understood that the operation of the system of this invention does not require that the upper and lower limit settings come into play during exercise. The settings of one or both could be put at a point that they are outside the angle achievable by the patient during exercise so that the patient can achieve full extension and flexion of the involved joint. Alternatively, a limit might be set only on flexion or extension, leaving the other motion direction free of limit restraint.

It should be apparent that an alternative embodiment of the invention could involve elimination of the controlled stop portion of the system and provide only for the sounding of the buzzer when the limit is reached. It should also be apparent that the controlled stop feature is itself an optional, albeit highly advantageous, feature of the invention and the principal advantages of the invention could be achieved without incorporating it in the system. The same is true of the acceleration limit circuit, i.e. it is an optional feature of the invention which is very advantageous, but the principal advantages of the invention would be achieved in a system which eliminated that feature.

FIG. 8 of the drawings illustrates the detailed circuitry of a presently preferred embodiment of valve position control circuitry 62, which in this version of the invention includes a linearizer circuit which functions to linearize the control of the maximum permitted rotational velocity for accurate setting of the same by the velocity set potentiometer. There are various sources of nonlinearity in the overall system which would cause the maximum velocity setting to be inaccurate if a linear potentiometer setting scale is used in an analog system as shown in the embodiment of FIGS. 4-9. One of the main sources of nonlinearity is in the proportional valve control of permitted hydraulic flow rate, but other sources of nonlinearity may involve nonlinearity in the analog computer circuit elements. The function of the linearizer circuitry, involving the circuit elements 120, 122, and 124 and related circuitry will be described below after a description of the basic solenoid position control circuitry shown in FIG. 7.

The position of the valve piston in the solenoid controlled valve 67 (FIG. 5), is controlled by the duty cycle of a rectangular waveform signal which is applied to the control winding of the solenoid. The electrical drive of the solenoid is opposed by a tension spring pulling in opposite sense on the valve piston. Applying a variable duty cycle rectangular signal to the solenoid winding controls the amount of average energization of the position control winding and thus the position that the piston will assume and the orifice size of the valve. To avoid overshoot and other troublesome characteristics of the proportional solenoid valve, it is preferable to monitor the actual position of the valve piston and feed back the position signal into the position control circuit as a servo control on valve positon. For the presently preferred embodiment of this invention, a proportional solenoid valve available from Ledex Corporation (Part No. 160001-004) is employed. This valve system has built into it positon sensing primary and secondary windings which may be used to monitor valve piston position.

Referring now to FIG. 7, it is seen that the output of the linearizer circuit on lead 125 is summed at the input of a position error summing circuit 129 with a position signal from position detector circuit 65. The linearized demand velocity signal VDL and the valve position signal P have respective opposite polarities so that the output of the position error summing circuit 129 is a position error signal whose value is dependent upon the value of the signal VDL as well as the position signal P. This signal can also be considered to be the linearized demand velocity signal VDL on which a position error signal has been impressed. The value of this position error signal is fed to the plus input of comparator 131 and the minus input is coupled to the output of a sawtooth oscillator circuit 130. The output of the comparator circuit 131 is thus a rectangular waveform with a duty cycle controlled by the value of the position error signal. Ths rectangular waveform signal is fed to a power field effect transistor 132 which is turned on and off by the signal to apply twelve volts to the solenoid winding during the on portion of the transistor operating cycle. The sawtooth oscillator may conveniently be operated at a frequency in the range of 0.2 to 1 kHz.

The proportional solenoid includes a transformer system including a primary winding PRI and a pair of secondary windings SEC1 and SEC2 which are coupled in complementary manner to the primary winding. Thus, for a fixed AC signal input to the primary winding the output from the secondary windings coupled in series as shown will be a signal proportional to solenoid position. The primary winding is coupled to a square wave oscillator 134 through an amplifier circuit 135. The output of the square wave oscillator 134 also operates signal sampling gates A and B within gate circuit 137 to sample the value of the signal output from the secondary windings through unity gain amplifier 136. The sampled signal is stored in hold circuit 138 and fed to summing circuit 129. The square wave oscillator 134 may operate at a frequency in the range of 2 to 10 kHz.

The linearizing circuit shown in FIG. 8 basically uses a freerunning analog-to-digital converter (ADC) 120 to convert the value of the velocity demand signal VD on lead 61 to an eight bit digital word on bus 121. This eight bit digital word addresses an eight bit data word stored in programmable read only memory (PROM) 122 which is then output on data bus 123. The eight bit data word on bus 123 is coupled to digital-to-analog converter (DAC) 124 wherein the digital word value is converted back to an analog voltage. DAC 124 includes internal data latches which are signalled to load a new data word from the PROM 122 on each cycle of ADC 120 when valid data is present. This load signal is provided through logic circuit 126.

Comparator circuit 127 provides a stable reference voltage to ADC 120 and DAC 124. The input circuit 128 receives the S signal from the range limit circuit of FIG. 6 and couples it as an address signal to PROM 122 so that the portion of PROM 122 addressed during movement of the lever arm in one direction is different from the portion addressed during movement of the lever arm in the opposite direction. This provides for different linearization values to be stored in the PROM for the different directions which is uselful since it has been observed that the nonlinearities present are different in the two directions of motion.

The data word values which are stored in PROM 122 are derived from running calibration tests on each separate manufactured unit of the system of this invention so that the individual nonlinearities of the particular components utilized in that unit will be eliminated. The calibration tests involve making measurements at a plurality of velocity control settings over the setting range of what the velocity demand signal VD actually is at that setting when the lever arm is moving at that velocity as compared to the signal which must be fed to the summing circuit 129 to achieve that maximum permitted velocity from the hydraulic system and its control circuitry. These data points are then used, with appropriate linear interpolation between points, to determine two hundred and fifty six data words to store in the PROM 122 to convert values of the VD signal to appropriate corrected signal values VDC.

FIG. 8 illustrates the torque measuring circuitry utilized in a presently preferred analog computer version of this invention. Strain gages 72 and 73 are monolithic semiconductor strain gages which may be Foxboro strain gages (Model No. 900). These strain gages are connected in opposite polarity to their respective output signal conditioning circuits 141 and 142. Circuits 139 and 140 are constant current drive circuits for the strain gages. The conditioned outputs of the strain gages are summed in circuit 143 to develop the calibrated torque signal which is fed through the inverting circuit 144 or directly as the torque output signal T depending upon the setting of the left/right switch 45B.

The strain gages 72,73 measure the pressure in the two bidirectional hydraulic fluid lines between the rotatry actuator 71 and the bidirectional flow controller 69 shown in FIG. 5. This measures the pressure in each chamber of the actuator and the pressure difference between the two chambers is proportional to the torque applied by the patient to the lever arm, except for a small error due to friction in the actuator.

Since the torque measurement is utitlized in the range limit control circuitry as part of the logic which actuates and releases the braking signal circuit, it is important to have a stable torque signal baseline, i.e. a zero value of the torque signal in absence of applied torque in either direction. Accordingly the circuitry of FIG. 9 incorporates an automatic baseline calibration system which operates when the lever arm is quiescent for a several seconds to readjust the baseline to a zero reading.

A differentiator circuit 145 is used to determine when there is motion of the lever arm and thus some variation in the torque signal output. The output of differentiator circuit 145 is coupled through an absolute value circuit 146 into a comparator circuit 146A with a threshold established by a single diode drop (about 0.6 volts) so that the comparator is triggered by any significant change in torque value which in turn indicates that the lever arm is in motion. The output of the comparator 146A operates gate B in gating circuit 147 to reset timer 148 and thus keep it from closing gate A to couple the torque output signal value into the baseline setting circuitry.

However, during a quiescent condition of the lever arm, the timer circuit 148 will time out and close the gate A. Any nonzero output value of the torque signal at such time is detected in comparator 149 and fed as a baseline error signal to integrator 150 whose output changes in a direction to reduce the detected error. When gate A is later opened the signal value at the output of integrator remains constant as the current baseline correction value fed back to the difference circuit 143.

Referring now to FIGS. 11-13, the structure and function of rotary actuator 71, bidirectional flow controller 69 and solenoid operated flow control valve 67 will be described. Solenoid flow valve 67 includes a proportional solenoid operating to control the position of a valve piston 204 which slidably traverses a channel 206 within valve body 200 in a metal to metal sealing relationship with highly accurately machined surfaces. The movement of piston 204 is resisted by compression spring 205 which extends through flow channel 208. The end of sliding piston 204 defines the size of a flow orfice between channel 208 and channel 206. Fluid ports 201 and 202 are provided in the side of the valve body 200 to communicate hydraulic fluid to and from the respective channels 206 and 208.

Bidirectional flow controller 69 includes a valve body 180 which is provided with an internal channel 195 in which a valve piston 183 is slidably received with a metal to metal seal between the channel 195 and the outer surface 194 of piston 183. The piston 183 is mounted to a hollow shaft 193 which rides on a solid shaft 186 extending between end caps 184 and 185 with the respective slidably engaged surfaces providing a metal to metal seal. Compression springs 191 and 192 are carried on shaft 186 between the end caps and the piston to bias the piston toward a central position. The respective ends of the piston 183 define together with channels 187 and 188 a pair of flow orfices 196 and 197 whose sizes are determined by the position of piston 183. Fluid ports 181 and 182 communicate hydraulic fluid to channels 187 and 188 and fluid ports 189 and 190 communicate fluid to and from the other sides of the orfices 196 and 197.

Rotary actuator 71 includes an actuator housing 160 with end caps 161 and 162 mounted thereto to form an internal cavity. Shaft 168 extends through the internal cavity of the actuator and is journaled for rotation in bearings 169 mounted in each of the end caps. O-ring seals 170 and 171 provide fluid tight sealing for the end caps to the actuator housing and for the rotating shaft to the end caps. A stationary vane 163 is mounted to the top internal surface of the actuator housing while a rotating vane 172 is carried in a keyway on shaft 168.

The bottom surface 172A of rotating vane 172 is accurately machined to fit the contour of the inner surface of the housing to form a close fit metal to metal seal. The ends of the rotating vane are similarly machined to provide a close metal to metal seal against the inner surfaces of the end caps. The bottom surface 163A of the stationary vane 163 is machined to give a close tolerance sliding fit with the exterior surface of the shaft 168 as it rotates. The stationary vane 163 and the rotating shaft 168 together with the rotating vane 172 divide the interior of the actuator into two separate fluid compartments 160A and 160B.

Ports 164 and 165 extend through the top wall of housing 160 to communicate with ports 166 and 167 which extend through the stationary vane and communicate with the two internal compartments. The actuator relies on accurately machined surfaces for the internal surfaces which move relative to each other as the shaft and vane rotate to give a low parasitic friction in the actuator. Mounting apertures 174 are provided for mounting pressure transducers to the actuator body with an appropriate channel into the ports 164 and 165 to communicate the fluid pressure from the internal chambers 160A and 160B to the two pressure transducers. Potentiometer 28 is preferably mounted to the back of the shaft to detect shaft rotation angle.

The bidirectional flow controller 69 mounts directly on the top surface of actuator housing 160 with the ports 181 and 182 aligned with the ports 164 and 165. Appropriate O-ring seals and mounting screws (not shown) may be employed to mount these two components together with a fluid tight seal between the ports. The solenoid valve assembly 67 is mounted to the side of the bidirectional flow controller 69 with the ports 201 and 202 aligned with the ports 189 and 190. These two components may be fastened together using an arrangement of mounting screws and with O-ring seals (not shown) at the ports to provide a fluid tight coupling of the two elements.

The overall operation of these hydraulic components is as follows. The position of the piston 204 of the solenoid proportional control valve 67 is set by the velocity demand signal and thus produces a particular orfice size which regulates the rate of flow of hydraulic fluid through the valve. This regulation provides a main and essential portion of the flow regulation which sets a maximum permitted rotational velocity for the actuator shaft 168. However, under high torque conditions the proportional valve itself with the accompanying feedback control circuitry (velocity computation and servoing with the velocity demand signal) cannot provide stable regulation of the maximum permitted angular velocity. Thus, the bidirectional flow controller is included to assist in regulating the flow under high torque conditions.

The bidirectional flow controller is designed such that it will have no regulating effect until the back pressure which is built up behind the orfice in the proportional control valve has reached a certain valve such as, for example, about five pounds per square inch. Until such a pressure differential between chambers 196 and 197 has built up, the compression springs maintain the valve piston in a central position. After the threshold pressure of the controller has been exceeded due to the torque on the actuator shaft attempting to move oil at a faster rate through the restricted orfice of the valve, the controller piston 183 begins to shift in the direction of the low pressure side of the controller. This produces a partial occlusion of the orfice on the lower pressure side of the controller which assists in restricting the increase in oil flow which the increased torque is attempting to produce.

The controller thus assists in resisting acceleration of the actuator shaft as the torque applied thereto increases beyond the capacity of the proportional valve and feedback system to control it with stability. The piston 183 of the regulator will assume a position which responds to the pressure differential on both ends thereof with sensitive response to changes in torque and resulting fluid backpressure changes. The controller 69 itself provides a servo type control, i.e. it responds to an error signal in the form of increased back pressure on one side to restrict flow on the other side which, in turn, restricts flow on the other side so that pressure builds on that side of the controller. Increased torque tending to increase fluid flow and permit acceleration to a velocity exceeding the maximum permitted velocity is resisted by further flow restriction which resists the acceleration of the actuator shaft.

The combination of hydraulic servo regulation of the flow together with the inner and outer servo feedback loops in the electronic control circuitry provides highly stable and accurate control of the maximum permitted angular velocity of the actuator shaft. This together with the linearizer circuitry provides a degree of accuracy of setting and control of isokinetic velocity which is not achieved by prior art systems.

It should be understood that, although the hydraulic system described above is the preferred embodiment of a rotational veloctiy governor system, there are other type of velocity governor systems which could be employed to achieve essentially the same function, but not necessarily with the same degree of performance or at the same cost for equivalent performance. For example, a motor and gearbox arrangement with control of motor torque resisting the rotation of the lever arm through the mechanical advantage of the gear box could be employed, but such a system would be more costly and would tend to have more parasitic drag on initial acceleration of the lever arm. Some of the velocity governor systems disclosed in the above-referenced Perrine patent could also be utilized, but they similarly would not have the cost/performance benefits of the hydraulic actuator-controller-valve system described above.

It should also be understood that the system of this invention could utilized a different approach to positioning the proportional control valve such as, for example, using a bidirectional stepping motor with a similar feedback of detected valve position if necessary. FIG. 13 illustrates that the velocity control computer system of this invention may also be implemented in the form of a microprocessor-based, real time digital control system. Most of the elements shown in FIG. 13 are elements of a standard microprocessor based computer system. In such a system microprocessor and support circuits 220 communicate with program memory 224, data memory 225, and input/output ports 226 over address bus 221, data bus 222, and control bus 223. It is also standard to interface the microcomputer system to various input/output devices, such as keyboard and display 229, printer 230, and a data communication channel 232. In the real time control and data aquisition usage of a microcomputer, it is standard for the microcomputer to use the combination of an analog signal multiplexer 227 and an analog to digital converter 228 to acquire measurement and control parameters of the system being controlled. It is also standard to use a digital to analog converter 231 to communicate control signals to the system being controlled.

To utilize a microcomputer as the velocity control computer in the general system embodiment of FIG. 1, the angle signal A, lever arm length signal L1 and the two torque signals T1 and T2 are provided as inputs to the analog multiplexer 227. The anatomical lever length L2, the command velocity value V, the range limits U and L, and the left/right control information would all be entered into the computer system via keyboard and display 229.

The microcomputer system is programmed to perform essentially the same functions in a digital computational sense as the analog computer circuitry of FIGS. 6–9 performs in a continuous analog manner. In the digital control system, however, the computational resources of the computer are time-shared amoung the various functions that must be performed to provide the overall real time control of the exercise system. Since the digital computer is able to make computations very rapidly, this time sharing of resources is practicable and the digital computer will maintain the same degree of real time control as the on-line analog computer system.

In addition, implementation of the velocity control computer in the form of a digital computer system provides additional data processing and real time control possibilities. It is a simple matter, for example, for the digital computer system to calculate on a continuous basis the accumulated work performed during the exercise motion, and this calculation can be performed separately for the muscle groups involved in flexion and extension, if desired. The computer can be programmed to calculate and display to the patient the peak torque being developed during the exercise motion. It can be programmed to determine the maximum range of motion of the involved joint by detecting the angle peak values and this range of motion calculation can be averaged over several exercise motions.

Employment of a digital computer system permits a variety of anatomical demand velocity functions to be experimented with to determine whether variations from isokinetic anatomical rotation would be preferable for certain rehabilitation situations or for certain human performance improvement exercise regimens. For example, an isometric hold could be programmed into the anatomical velocity demand function at the point that the muscle group is developing peak torque and this could be implemented on the basis that the computer itself determines the angle value at which the velocity demand signal should go to zero for the isometric hold on the basis of actual torque versus angle measurements made on one or more trial exercise motions. As another example, sine wave velocity control functions could be used to increase or decrease the maximum permitted angular velocity during the midrange of the exercise motion. These functions could also be set up based on trial exercise runs which provide data on the total range of motion of the joint.

Implementation of the velocity control computer in the form of a digital computer system will greatly enhance the processing of data related to the exercise performed on the system during the individual exercise bout as well as over the time span of a rehabilitation or muscle training program. Ultimately, exercise regimens may be set up for a particular rehabilitation program for an individual patient and the computer system will automatically follow the regimen from one exercise session to the next, each time tracking and reporting whether the anticipated progress is being achieved so that adjustments can be made in the regimen as necessary. This can be accomplished by downloading the control variables to the computer for the individual patient based solely on the input of the patient number. This would avoid repetitive measurement and entry of patient limb length and the other control variables required by the system.

The various embodiments of an exercise system in accordance with this invention which are described above are given by way of example only and it should be understood that persons of skill in the various arts involved in this invention could make numerous modifications therein without departing from the scope of this invention as claimed in the following claims.

What is claimed is:

1. In a muscle exercise and diagnostic system, a lever arm; means mounting said lever arm for rotation about a fixed axis; connecting means for connecting a selected portion of the human body to said lever arm for rotation with said lever arm about a selected anatomical axis of rotation, including mounting means establishing between said lever arm and said body portion a fixed tangential mounting relation and a sliding radial mounting relation along the axis of the lever arm to permit free radial movement therebetween during an exercise motion of said human body portion; velocity control means operatively associated with said lever arm for limiting the maximum permitted rotational velocity of said arm to a value predetermined in accordance with a preselected velocity control function which includes measured values of the distances from said point of attachment to said anatomical axis and to said fixed axis, and means for inputting said measured values to said velocity control means.

2. The apparatus of claim 1, further comprising angle means for registering the angle of said lever arm and wherein said velocity control means further comprises motion limitation means responsive to an input angle limit value and said registered angle value to limit the angular rotation of said arm to be less than said angle limit value.

3. The apparatus of claim 1, wherein said velocity control means includes a rotational velocity governor system comprising a rotary hydraulic actuator with a rotationally mounted shaft extending therethrough and carrying a rotating vane cooperating with a stationary vane an the interior of said actuator to define two complementarily variable volumetric chambers on opposite sides of said vanes and a pair of fluid ports communicating with said chambers, said lever arm being mounted to said shaft; a proportional fluid control valve having a pair of fluid ports communicating with said actuator fluid ports and valve means responsive to an input control signal to control an orfice size for fluid communicated between said actuator fluid ports; and a bidirectional flow controller interposed between said actuator fluid ports and said valve fluid ports and having a pair of flow channels on opposite sides thereof, a piston slidably mounted between said flow channels for controlling the relative sizes of said flow channels depending on the relative postion thereof, said piston being spring biased toward a central position and being responsive to a fluid pressure differential between said flow channels exceeding a prearranged threshold value to move in the direction of said pressure differential to partially occlude one of said fluid passages and thereby to assist in resisting the passage of fluid from one of said actuator chambers to the other as said lever arm is rotated with high applied torque.

4. The apparatus of claim 1, wherein said mounting means provides a fixed connection to said body portion and a radially sliding connection to said lever arm, and said means for inputting comprises means associated with said mounting means for registering the distance from said fixed connection to said fixed axis and supplying said registered distance value to said velocity control means, and means for manually inputting into said velocity control means a measured value of the distance from said fixed connection to said anatomical axis.

5. The apparatus of claim 4, further comprising means establishing an anatomical velocity demand function; said velocity control means including a rotational velocity governor system responsive to an input velocity control signal to limit the maximum permitted instantaneous rotational velocity of said lever arm; and velocity control computer means for supplying said velocity control signal as a prearranged function of said anatomical velocity demand function and said measured values of the distances from said point of attachment to said anatomical axis and to said fixed axis.

6. The apparatus of claim 5, further comprising velocity measuring means for determining the instantaneous actual rotational velocity of said lever arm and providing an actual velocity signal corresponding thereto; and said prearranged function of said velocity control computer means includes said actual velocity signal.

7. The apparatus of claim 5, further comprising angle measuring means for registering the angle of said lever arm; and said velocity control computer means includes limit detecting means for detecting when said measured angle value is equal to a preset angle limit value and thereupon supplying a prearranged braking functional signal; and said prearranged function includes said braking functional signal.

8. The apparatus of claim 5, wherein said velocity computer means supplies said velocity control signal as a prearranged acceleration limit function during initial acceleration of said lever arm toward said maximum permitted instantaneous velocity.

9. The apparatus of claim 5, wherein said means establishing an anatomical velocity demand function comprises a potentiometer for setting a preselected constant maximum angular velocity of said body portion about said anatomical axis; said velocity control means includes a first variable resistance with a resistance control knob setting calibrated to the distance from said point of attachment to said anatomical axis; a second variable resistance having a control coupled to said connecting means and calibrated to register the instantaneous distance from said point of attachment to said fixed axis of rotation; a ratio circuit coupled to said first and second variable resistances for supplying an output electrical signal having an value corresponding to the ratio of said lever arm length to said anatomical lever length, said output signal being supplied to said potentiometer to produce a demand velocity control signal which varies with said lever arm length.

10. The apparatus of claim 9, further comprising an angle potentiometer coupled to said mounting means for registering the angle of said lever arm; and said velocity control computer means further comprises velocity circuit means for deriving an actual velocity signal from said angle potentiometer; and combining circuit means for producing a velocity control signal as a combined function of said demand velocity control signal and said actual velocity signal.

11. The apparatus of claim 10, further comprising a minimum value circuit at the output of said combining circuit and an acceleration limit circuit receiving said actual velocity signal and supplying to said minimum value circuit an acceleration control signal having a value incrementally larger than said actual velocity signal so that initial acceleration of said lever arm is limited and accomodating resistance to acceleration is perceived from the start of lever arm motion.

12. The apparatus of claim 10, wherein said rotational velocity governor system comprises a rotary hydraulic actuator with a rotationally mounted shaft extending therethrough and carrying a rotating vane cooperating with a stationary vane an the interior of said actuator to define two complementarily variable volumetric chambers on opposite sides of said vanes. and a pair of fluid ports communicating with said chambers, said lever arm being mounted to said shaft; a proportional fluid control valve having a pair of fluid port communicating with said actuator fluid ports and value means responsive to an input control signal to control an orfice size for fluid communicated between said actuator fluid ports; and a bidirectional flow controller interposed between said actuator fluid ports and said valve fluid ports and having a pair of flow channels on opposite sides thereof, a piston slidably mounted between said flow channels for controlling the relative sizes of said flow channels depending on the relative position thereof, said piston being spring biased toward a central position and being responsive to a fluid pressure differential between said flow channels exceeding a prearranged threshold value to move in the direction of said pressure differential to partially occlude one of said fluid passages and thereby to assist in resisting the passage of fluid from one of said actuator chambers to the other as said lever arm is rotated with high applied torque; said proportional fluid control valve is a solenoid controlled valve; and said velocity control computer means further comprises valve driver circuit means for supplying a rectangular waveform driving signal to said solenoid having a duty cycle modulated by the valve of an error signal for controlling valve position; circuit means operative associated with said solenoid valve for deriving an electrical signal indicating the position of said valve; and error signal computing means combining said velocity control signal and said position signal to produce said error signal for servo control of said valve position.

13. The apparatus of claim 12, further comprising a linearizer circuit interposed between said minimum value circuit and said error computing circuit means for translating input velocity control signal values into corrected velocity control signal values based on correction factors predetermined from actual velocity measurements during a calibration operation on said system.

14. In a method for controlled accommodating resistance exercise, the steps of:
mounting a lever arm for rotation about a fixed axis;
disposing a human body attachment device on said lever arm in a tangentially fixed and radially movable mounting relation along the axis of the lever arm to permit free radial movement of said connecting means relative to said fixed axis during an exercise motion of said human body portion;
contacting said attachment device with a selected portion of the human body for rotation of said attachment device and lever arm with said body portion about an anatomical axis of rotation;
measuring the lever arm radius from said attachment device to said fixed axis of rotation;
measuring the anatomical radius from said attachment device to said anatomical axis of rotation; and
restraining rotation of said lever arm to an angular velocity less than or equal to a value predetermined in accordance with a preselected velocity control function which includes the measured lever arm radius and the measured anatomical radius.

15. The method of claim 14, wherein said step of measuring the lever arm radius comprises constantly monitoring the lever arm radius value as said body portion traverses a rotational exercise path; and said step of restraining rotation of said lever arm is performed in accordance with a time varying velocity control function which includes the time-varying lever arm radius.

16. The method of claim 15, wherein said preselected velocity control function provides a substantially constant maximum angular velocity of rotation of said body portion about said anatomical axis of rotation by adjusting the maximum permitted angular velocity of rotation of said lever arm about said fixed axis in response to changes in said monitored lever arm length.

17. The method of claim 14, wherein said preselected velocity control function is prearranged to provide a substantially constant maximum angular velocity of rotation of said body portion about said anatomical axis of rotation.

18. In a muscle exercise system, a lever arm; means mounting said lever arm for rotation about a fixed axis; connecting means for connecting a selected portion of the human body to said lever arm for rotation with said lever arm about a selected anatomical axis of rotation, including mounting means establishing between said lever arm and said body portion a fixed tangential mounting relation and sliding radial mounting relation along the axis of the lever arm to permit free radial movement therebetween during an exercise motion of said human body portion; and velocity control means coupled to said lever arm for limiting the maximum permitted rotational velocity of said arm.

19. The system of claim 18, wherein said mounting means provides a fixed connection to said body portion and a radially sliding connection to said lever arm.

20. In a method for controlled accommodating resistance exercise, the steps of:
mounting a lever arm for rotation about a fixed axis;
disposing a human body attachment device on said lever arm in a tangentially fixed and radially movable mounting relation along the axis of the lever arm to permit free radial movement of said connecting means relative to said fixed axis during an exercise motion;
contacting said attachment device with a selected portion of the human body for rotation of said attachment device and lever arm with said body portion about an anatomical axis of rotation; and
restraining rotation of said lever arm to an angular velocity less than or equal to a maximum value.

* * * * *

UNITED STATES PATENT AND TRADEMARK OFFICE
CERTIFICATE OF CORRECTION

PATENT NO. : 4,601,468
DATED : July 22, 1986
INVENTOR(S) : Malcolm L. Bond, Philip T. Dempster It is certified that error appears in the above-identified patent and that said Letters Patent are hereby corrected as shown below:

On front of patent at [73] Assignee:, change name of Assignee to Loredan Biomedical, Inc.

Signed and Sealed this

Sixth Day of January, 1987

*Attest:*

DONALD J. QUIGG

*Attesting Officer*  *Commissioner of Patents and Trademarks*